US007962303B2

(12) United States Patent
Oue et al.

(10) Patent No.: US 7,962,303 B2
(45) Date of Patent: Jun. 14, 2011

(54) DISTORTION EVALUATING APPARATUS AND DISTORTION EVALUATING METHOD

(75) Inventors: Seiji Oue, Takarazuka (JP); Hideto Katsuma, Takarazuka (JP); Yoichi Tachi, Toyonaka (JP); Kotaro Ikeda, Takarazuka (JP); Shinya Nakasaku, Hyogo (JP)

(73) Assignee: Daihatsu Motor Co., Ltd., Osaka (JP)

( * ) Notice: Subject to any disclaimer, the term of this patent is extended or adjusted under 35 U.S.C. 154(b) by 284 days.

(21) Appl. No.: 12/064,699

(22) PCT Filed: Jul. 11, 2006

(86) PCT No.: PCT/JP2006/313771
§ 371 (c)(1),
(2), (4) Date: Mar. 4, 2009

(87) PCT Pub. No.: WO2007/026467
PCT Pub. Date: Mar. 8, 2007

(65) Prior Publication Data
US 2009/0171622 A1   Jul. 2, 2009

(30) Foreign Application Priority Data
Aug. 30, 2005  (JP) ................. 2005-249129

(51) Int. Cl.
*G06F 15/00* (2006.01)
*G01B 21/20* (2006.01)
(52) U.S. Cl. ........................... 702/88; 702/167

(58) Field of Classification Search .............. 702/88, 702/167, 182
See application file for complete search history.

(56) References Cited

U.S. PATENT DOCUMENTS
5,844,801 A   12/1998  Kodama et al.
6,125,198 A * 9/2000  Onda .................. 382/154

FOREIGN PATENT DOCUMENTS
| JP | 07110226 A | 4/1995 |
| JP | 08159740 A | 6/1996 |
| JP | 3015615 B2 | 3/2000 |
| JP | 2002257528 A | 9/2002 |
| JP | 2004317495 A | 11/2004 |

* cited by examiner

*Primary Examiner* — Bryan Bui
(74) *Attorney, Agent, or Firm* — The Webb Law Firm

(57) ABSTRACT

A distortion evaluating apparatus which can quantitatively evaluate distortion in a measurement object surface is provided. A distortion evaluating apparatus evaluates distortion based on three-dimensional measurement data obtained from a measurement object surface. The apparatus includes a secondary differential component adapted for effecting a secondary differential operation on two-dimensional measurement data of a cross section of the measurement object surface indicative of unevenness therein, thus obtaining curvature data of the cross section, a permissible range setting component adapted for setting a permissible range for the curvature data, based on range of an upper limit value and a lower limit value from a reference value, and a distortion data extracting means component adapted for extracting a portion of the curvature data exceeding the set permissible range as distortion data indicative of the distortion in the cross section.

6 Claims, 7 Drawing Sheets

(a) photographic image    (b) measurement image (a)

(b)

(a)

(b)

DISTORTION EVALUATING APPARATUS AND DISTORTION EVALUATING METHOD

BACKGROUND OF THE INVENTION

1. Technical Field

The present invention relates to an apparatus and a method for evaluating distortion based on three-dimensional measurement data obtained from a measurement object surface.

2. Background Art

In a body surface such as a surface of a door panel of a motorcar manufactured with using a steel plate, there sometimes can develop a shape different from an originally designed shape (i.e. distortion), due to the thickness and/or composition of the steel plate used. And, determination of whether the distortion is within an acceptable range or not is effected through sensory evaluation by a skilled artisan. However, this determination cannot be made appropriately under a predetermined standard, unless the artisan is an experienced one who has actually observed various distortions. For this reason, there has been proposed a distortion evaluating apparatus designed to extract mechanically a certain characteristics from the distortion in the measurement object surface such as a body surface, thereby effecting the sensory evaluation of distortion degree in a quantitative manner.

According to a technique employed by a distortion evaluating apparatus described in Patent Document 1, a secondary differential operation is carried out on two-dimensional measurement data of a cross section of the measurement object surface, indicative of unevenness of the surface and then e.g. a difference value between the maximum value and the minimum value of the secondary differential values, as the characteristics indicative of the distortion. Thereafter, this difference value is assigned into a prediction formula, by which a distortion evaluation value is predicted. More particularly, a difference between a cross section shape line of the measurement object surface actually determined and an ideal curve of values which comprise e.g. design data per se is calculated, thus obtaining a surface distortion line including all large and small distortions which have developed in the measurement object surface. Then, a secondary differential operation is effected on this surface distortion line obtained with including all large and small distortions, and a difference value between the maximum value and the minimum value of the resultant secondary differential values is utilized for the distortion evaluation. The secondary differential values of this two-dimensional measurement data (surface distortion line) correspond to curvature data of the cross section of the measurement object surface. And, it may be determined that the greater the absolute value of the secondary differential value, the greater the distortion.

Patent Document 1: Japanese Patent No. 3015615

According to the distortion evaluating apparatus described in Patent Document 1, the apparatus employs a difference value between the maximum value and the minimum value of two-dimensional measurement data, as a characteristics used for distortion degree evaluation. This means that the apparatus employs data including all, i.e. large and small distortions present in the measurement object surface, for the purpose of distortion evaluation of the measurement object surface. In the case of a sensory evaluation by a human, on the other hand, even when a distortion exists, this may sometimes be determined as permissible if it is not conspicuous. On the other hand, in the case of the conventional method using the secondary differential values of two-dimensional measurement data as they are, without effecting any data processing thereon, the method is configured to take note of and find problematic even such small distortion also which would be found permissible by a sensory evaluation by a human.

Further, if the absolute value of a secondary differential value is large, this should be determined appropriately as being indicative of a large distortion. However, such appropriate evaluation may sometimes be not done by the distortion evaluating apparatus disclosed in Patent Document 1. For instance, a certain waveform can have a large peak (maximum value) of absolute value in the positive direction and has a small peak (minimum value) of absolute value in the negative direction. Another waveform can have equal peaks (maximum value and minimum value) of absolute value in the positive direction and negative direction. Still another waveform can have a small peak (minimum value) of absolute value in the positive direction and has a large peak (maximum value) of absolute value in the negative direction. In such case, the distortion evaluating apparatus described in Patent Document 1 would provide a same distortion evaluation result for all of these three kinds of waveforms as long as the difference value between the maximum value and the minimum value of the secondary differential values is the same.

Therefore, the distortion evaluation result obtained by the conventional distortion evaluating apparatus would be different from the desirable result which could be obtained by the human sensory evaluation. Hence, it cannot be said that this conventional apparatus really effects quantitative evaluation of distortion in a measurement object surface.

Moreover, the original shape of the measurement object surface to be used as the baseline can sometimes be deformed by the spring-back phenomenon of the steel plate, so that the cross section line obtained therefrom may deviate from the design data. In this case, the conventional method would determine such original shape of the measurement object surface too as "distortion", which actually is not. More particularly, the distortion evaluating apparatus disclosed in Patent Document 1 is configured to attempt to calculate difference values between a cross section shape line and an ideal curve so as to obtain a surface distortion line which includes only the distortions which have developed in the measurement object surface. As a matter of fact, the above difference values include not only the distortions, but also the original shape of the measurement object surface. Moreover, even if no distortion has actually developed, there is the possibility of the original shape of the measurement object surface formed by the spring back being determined as a distortion erroneously.

In addition, in the case of the distortion evaluating apparatus described in Patent Document 1, the apparatus monitors the secondary differential values and calculates a difference value between the maximum and minimum values thereof. Hence, there is another problem of the apparatus being constantly under a computational load over a predetermined level.

The present invention has been made in view of the above-described problem. And, its object is to provide an apparatus and a method for evaluating distortion which can quantitatively evaluate distortion in a measurement object surface.

SUMMARY OF THE INVENTION

According to a characterizing construction of a distortion evaluating apparatus relating to the present invention for accomplishing the above-noted object, a distortion evaluating apparatus for evaluating distortion based on three-dimensional measurement data obtained from a measurement object surface, the apparatus comprises:

secondary differential component adapted for effecting a secondary differential operation on two-dimensional measurement data of a cross section of the measurement object surface indicative of unevenness therein, thus obtaining curvature data of the cross section;

a permissible range setting component adapted for setting a permissible range for said curvature data, based on range of an upper limit value and a lower limit value from a reference value; and a distortion data extracting component adapted for extracting a portion of said curvature data exceeding said set permissible range as distortion data indicative of the distortion in the cross section.

In the above, the curvature data of the cross section refer to data obtained by first effecting a differential operation on the two-dimension measurement data of the cross section thus obtaining slope data for each point of the cross section and then effecting a secondary differential operation on the slope data for each point of the cross section, so that the resultant data may indicate a change in the slopes of the cross section. For example, in the case of a cross section with a fixed curvature, such as a circle, the slope of the cross section changes by a fixed amount, so that the slope change amount of each point of the cross section will be constant. Whereas, in the case of a cross section with a plurality of different curvatures, such as a sine waveform, the slope change amount for each point in the cross section is not constant. As described above, the secondary differential component extracts the curvature data of the cross section by effecting a secondary differential operation on the two dimension measurement data of a predetermined cross section indicative of unevenness therein.

According to the above-described characterizing construction, the secondary differential component effects a secondary differential operation on two-dimensional measurement data of a cross section of the measurement object surface indicative of unevenness therein, thus obtaining curvature data of the cross section. The permissible range setting component sets a permissible range for said curvature data, based on range of an upper limit value and a lower limit value from a reference value. The distortion data extracting component extracts a portion of said curvature data exceeding said set permissible range as distortion data indicative of the distortion in the cross section. That is to say, the distortion evaluating apparatus having the above-described characterizing feature effects a data processing operation which does not determine curvature data with small absolute values within the set permissible range as any distortion. This data processing operation is identical to the above-described human sensory evaluation which disregards small distortions.

Further, as the permissible range setting component sets the permissible range for the curvature data, based on a range of an upper limit value and a lower limit value from a reference value, it is possible to set desirably which portion of the curvature data to be extracted as the distortion data. That is to say, even when the original shape of the measurement object surface has been deformed due to a spring back of the steel plate, by appropriately increasing/decreasing the reference value corresponding to the original shape in accordance with the deformed shape so that the increased/decreased reference value may be substantially equal to the secondary differential value of the cross section indicative of the original shape, it is possible not to erroneously determine the originally deformed shape due to the spring back as distortion.

In addition, as the distortion data extracting means is to effect only the comparison between the set permissible range with the curvature data in order to extract the distortion data, no significant computational load will be applied to the distortion evaluating apparatus.

As described above, the distortion data on which the inventive distortion evaluating apparatus effects the distortion evaluation is analogous to information on which a human worker effects his/her sensory evaluation. Hence, distortion in a measurement object surface can be evaluated quantitatively.

According to a further characterizing construction of the distortion evaluating apparatus relating to the present invention, said permissible range setting component changes at least one of said reference value, said upper limit value and said lower limit value, in accordance with a characteristics of said measurement object surface.

If the measurement object surface is flat, then, the secondary differential value of its cross section will be zero (the curvature data of the cross section will be zero). Whereas, if the cross section shape of the measurement object surface is curved originally, the curvature data of the cross section indicative of this cross section shape may exceed the set permissible range. In such case, even in the absence of any distortion, the curvature data of the cross section indicative of the original shape of the measurement object surface may be determined as distortion data erroneously.

Then, according to the above-described characterizing construction, as the permissible range setting component changes at least one of said reference value, said upper limit value and said lower limit value, in accordance with a characteristics of said measurement object surface, distortion which has actually developed in the measurement object surface can be extracted as distortion data selectively. As a result, distortion in a measurement object surface can be evaluated quantitatively.

According to a still further characterizing construction of the distortion evaluating apparatus relating to the present invention, said secondary differential component extracts said curvature data for each one of a plurality of cross sections over said measurement object surface three-dimensionally;

said distortion data extracting component includes a distortion degree evaluating component adapted for extracting said distortion data for each one of said cross sections three-dimensionally; and said distortion evaluating apparatus further comprises a distortion degree evaluating component adapted for evaluating a degree of distortion in a specific distorted region present in said measurement object surface, based on said three dimensional distortion data.

According to the above-described characterizing construction, as the distortion degree evaluating component evaluates a degree of distortion in a specific distorted region present in said measurement object surface, based on said three dimensional distortion data, it is possible to determine quantitatively a degree of distortion included in the three dimensional shape of the measurement object surface.

According to a still further characterizing construction of the distortion evaluating apparatus relating to the present invention, the apparatus further comprises a distortion length extracting component adapted for extracting the length of said specific distorted region based on three dimensional distortion data and a distortion volume extracting component adapted for extracting the volume of said specific distorted region based on the three dimensional distortion data; and said distortion degree evaluating component evaluates the degree of distortion in the specific distorted region by using the combination of the length and the volume of the specific distorted region as distortion evaluation data and comparing evaluation reference data and the distortion evaluation data with each other.

According to the above-described characterizing construction, the distortion length extracting component extracts the length of said specific distorted region based on the three dimensional distortion data and the distortion volume extracting component extracts the volume of said specific distorted region based on the three dimensional distortion data. And, the distortion degree evaluating component evaluates the degree of distortion in the specific distorted region by using the combination of the length and the volume of the specific distorted region as distortion evaluation data and comparing evaluation reference data and the distortion evaluation data with each other. Therefore, it is possible to determine quantitatively a degree of distortion included in the three dimensional shape of the measurement object surface, with using the characteristics (length and volume of the distorted region) included in the three dimensional distortion data of the measurement object surface.

According to a still further characterizing construction of the distortion evaluating apparatus relating to the present invention, the apparatus further comprises a distortion length extracting component adapted for extracting the length of said specific distorted region based on three dimensional distortion data and a distortion area extracting component adapted for extracting the area of said specific distorted region based on the three dimensional distortion data by integrating widths of the specific distorted region perpendicular to the length along the direction of this length; and said distortion degree evaluating component evaluates the degree of distortion in the specific distorted region by using the combination of said length and said area of the specific distorted region as distortion evaluation data and comparing evaluation reference data and said distortion evaluation data with each other.

According to the above-described characterizing construction, the distortion length extracting component extracts the length of said specific distorted region based on three dimensional distortion data and the distortion area extracting component extracts the area of said specific distorted region based on the three dimensional distortion data by integrating widths of the specific distorted region perpendicular to the length along the direction of this length. Then, the distortion degree evaluating component evaluates the degree of distortion in the specific distorted region by using the combination of said length and said area of the specific distorted region as distortion evaluation data and comparing evaluation reference data and the distortion evaluation data with each other. Therefore, it is possible to determine quantitatively a degree of distortion included in the three dimensional shape of the measurement object surface, with using the characteristics (length and area of the distorted region) included in the three dimensional distortion data of the measurement object surface.

According to a characterizing feature of a distortion evaluating method relating to the present invention for accomplishing the above-noted object, a distortion evaluating method for evaluating distortion based on three-dimensional measurement data obtained from a measurement object surface, the method comprises the steps of:

effecting a secondary differential operation on two-dimensional measurement data of a cross section of the measurement object surface indicative of unevenness therein, thus obtaining curvature data of the cross section;

setting a permissible range for said curvature data, based on a range of an upper limit value and a lower limit value from a reference value; and extracting a portion of said curvature data exceeding said set permissible range as distortion data indicative of the distortion in the cross section.

According to the above-described characterizing feature, a secondary differential operation is effected on two-dimensional measurement data of a cross section of the measurement object surface indicative of unevenness therein, thus obtaining curvature data of the cross section. The method sets a permissible range for said curvature data, based on a range of an upper limit value and a lower limit value from a reference value. Then, a portion of said curvature data exceeding said set permissible range is extracted as distortion data indicative of the distortion in the cross section. That is to say, the distortion evaluating method having the above-described characterizing feature effects a data processing operation which does not determine curvature data with small absolute values within the set permissible range as any distortion. This data processing operation is identical to the human sensory evaluation which disregards small distortions.

Further, as the method sets the permissible range for the curvature data, based on a range of an upper limit value and a lower limit value from a reference value, it is possible to set desirably which portion of the curvature data is to be extracted as the distortion data. That is to say, even when the original shape of the measurement object surface has been deformed due to a spring back of the steel plate, by appropriately increasing/decreasing the reference value corresponding to the original shape in accordance with the deformed shape so that the increased/decreased reference value may be substantially equal to the secondary differential value of the cross section indicative of the original shape, it is possible not to erroneously determine the originally deformed shape due to the spring back as distortion.

In addition, as the distortion data extraction involves only the comparison between the set permissible range with the curvature data for extracting the distortion data, there occurs no significant computational load.

As described above, the distortion data on which the inventive distortion evaluating method effects the distortion evaluation is analogous to information on which a human effects his/her sensory evaluation. Hence, distortion in a measurement object surface can be evaluated quantitatively.

DESCRIPTION OF THE PREFERRED EMBODIMENTS

First Embodiment

FIG. 1 shows a functional block diagram of a non-contact, three dimensional measurement system and a distortion evaluating apparatus 40 relating to a first embodiment of the present invention. This non-contact three dimensional measurement system is used for effecting non-contact, three-dimensional measurement of a shape of a door panel manufactured by press-working a steel plate in a mold. And, this three-dimensional measurement system includes a robot hand 10 as a measuring head moving means, a non-contact three-dimensional measuring means 20 for effecting checkered pattern analysis of a grating pattern photographic image projected on a measurement object surface while being shifted in phase under a tracking scanning of the door panel by the robot hand 10, thus obtaining three dimensional coordinate values for each pixel of the imaging image and outputting a measurement image with three dimensional distance data assigned to respective pixels thereof (More precisely, values of pixels constituting the image comprise the three dimensional distance data. Therefore, this image is different from an ordinary image, but will be referred to herein as "measurement image" for facilitating understanding), and a three dimensional measurement control unit 30 for processing measurement images of respective portions of the door panel transferred one after another from the non-contact three dimensional measuring means 20 and then generating three dimensional measurement data of the entire door panel. Also, the distortion evaluating apparatus 40 can be realized by combination of an arithmetic processing unit such as a computer and a predetermined program.

The robot hand 10 per se is a known device consisting essentially of an arm mechanism 11 having, at a leading end thereof a tool attaching portion 11$a$ which is movable three-dimensionally and a robot hand controller 12 for controlling the movements of this arm mechanism 11.

The non-contact three dimensional measuring means 20 includes a measuring head 21 having a checkered pattern projecting portion 21$a$ acting as a projector for projecting a grating pattern onto a measurement object surface and a camera portion 21$b$ for imaging a grating image which is deformed as being projected on the measurement object surface, a control portion 22 for controlling the checkered pattern projecting portion 21$a$, the camera portion 21$b$, etc. and a three dimensional distance data measuring portion 23 for analyzing the image transmitted from the camera portion 21$b$ and then generating and outputting the above-described measurement image. With such non-contact three dimensional measuring means 20, high precision measurement is made possible by combining the grating pattern projection with phase shift technique. The measuring principle and construction thereof are known and described in e.g. Japanese Patent Application "Kokai" No. 2004-317495 and Japanese Patent Application "Kokai" No. 2002-257528. As the measuring head 21 is attached to the tool attaching portion 11$a$ of the robot hand 10, the measuring head 21 can be moved to a desired position for effecting the three dimensional measurement.

Now, an explanation will be made with reference to FIG. 2 on the photographic image obtained by the camera portion 21$b$ and the measurement image corresponding to this photographic image. The photographic image shows a deformed grating pattern formed as the grating pattern projected onto the measurement object surface by the checkered pattern projecting portion 21$a$ is deformed due to shape change or curvature of the measurement object surface, the deformed grating pattern being shown as density variations which are pixel values of respective pixels constituting this photographic image. Then, by effecting an image analysis of the deformed grating pattern of this photographic image which varies according to variation in the shape of the measurement object surface, there are obtained three dimensional coordinate values of the respective pixel (this need not necessarily have one-to-one relationship with the pixel of the photographic image), that is, the three dimensional distance data. The data comprising the three dimensional distance data assigned instead of the density as the pixel value of each pixel is referred to as "measurement image" herein. For instance, a certain pixel Pn of the measurement image is to have three dimensional coordinate values (three dimensional distance data) as (Xn, Yn, Zn).

The three dimensional measurement data generated as above is then transferred from the three dimensional measurement control unit 30 to the distortion evaluating apparatus 40. Next, the construction of this distortion evaluating apparatus 40 and the distortion evaluating method effected with using the distortion evaluating apparatus 40 will be described.

As shown in FIG. 1, the distortion evaluating apparatus 40 includes a secondary differential means 41 for effecting a secondary differential operation on two-dimensional measurement data of a predetermined cross section of the measurement object surface indicative of unevenness therein, thus obtaining curvature data of the cross section, a permissible range setting means 43 for setting a permissible range for the curvature data, based on a range of an upper limit value and a lower limit value from a reference value, and a distortion data extracting means 42 for extracting a portion of the curvature data exceeding said set permissible range as distortion data indicative of the distortion in the cross section. The secondary differential means 41 obtains the curvature data of a plurality of respective cross sections over the measurement object surface three dimensionally.

As described above, the secondary differential means 41 is used for obtaining curvature data of cross sections. More particularly, when a differential operation is effected on two dimensional measurement data of a cross section, there is obtained slope data for each point in the cross section. Further, when a further differential operation is effected on this slope data for each point of the cross section, there is obtained slope change data. For example, in the case of a cross section with a fixed curvature, such as a circle, the slope of the cross section changes by a fixed amount, so that the slope change amount of each point of the cross section will be constant. Whereas, in the case of a cross section with a plurality of curvatures, such as a sine waveform, the slope change amount for each point in the cross section is not constant. As described above, it may be said that the secondary differential means 41 extracts the curvature data of the cross section by effecting a secondary differential operation on the two dimension measurement data of a predetermined cross section indicative of unevenness therein.

FIG. 3 shows distortion data to be described later in a grey scale corresponding to the magnitudes of values thereof. More particularly, the cross section curvature data obtained by the secondary differential means 41 are drawn three dimensionally for a plurality of mutually parallel cross sections of the measurement object surface. In this embodiment, a door handle attaching portion 2 is used as an example of the measurement object surface. As shown in FIG. 3, the door handle attaching portion 2 is laid laterally and there are developed distorted regions G1 through G4 at total four positions, i.e. at right and left ends and upper and lower positions of the attaching portion 2. FIG. 4 ($a$) shows a graph including a shape line (shown by a dot line) of a cross section A-A' at a position distant by a distance (a) in an upper direction (positive direction along the L-axis) from the door handle attaching portion 2 and curvature data (shown by a solid line) obtained as the result of the secondary differential operation on the two dimensional measurement data thereof. And, FIG. 4 ($b$) shows a graph including a shape line (shown by a dot line) of a cross section B-B' at a position distant by a distance (b) in the upper direction (positive direction along the L-axis) from the door handle attaching portion 2 and curvature data (shown by a solid line) obtained as the result of the secondary differential operation on the two dimensional measurement data thereof. In this, in FIG. 4, the respective curvature data comprises data (1/ρ) obtained by multiplying the data obtained by the secondary differential of the two dimensional measurement data of the cross section, with a value of "−1". And, "ρ" is the radius of the circumference forming the cross section. As described above, in this embodiment, since the values obtained by the secondary differential operation on the two dimensional measurement data are multiplied with the value "−1", if the cross section has an upwardly convex shape, the curvature of the portion of the cross section corresponding thereto will appear as an upwardly convex shape. Conversely, if the cross section has a downwardly convex shape, the curvature of the portion of the cross section corresponding thereto will appear as a downwardly convex shape correspondingly.

FIG. 4 shows also the set permissible range for the curvature data. This set permissible range is set by the permissible range setting means 43 as a range between an upper limit value and a lower limit value relative to a predetermined reference value. This set permissible range is used for extracting, from the above-described curvature data, distortion data indicative of distortion in the cross section.

The reference value is set, based on the original cross section shape of the measurement object surface. That is, the reference value can be a secondary differential value obtained by effecting a secondary differential operation on a cross section of the measurement object surface which is still free from any distortion. In this particular embodiment, as the curvature of the original measurement object surface of the attaching portion 2 is constant, the reference value is set as a constant value (especially, if the measurement object surface is a flat surface with zero curvature, the reference value can be set=0). Therefore, if no distortion occurs in the measurement object surface, the curvature data of the cross section will be equal to the reference value.

However, if a distortion develops in the measurement object surface, this causes deviation of the curvature data of the cross section from the reference value. More particularly, if a distortion with a small curvature occurs in the measurement object surface (i.e. a distortion with a gently varying slope at each point of the cross section), this will appear as a small amount of deviation of the curvature data of the cross section from the reference value. On the other hand, if a distortion with a large curvature occurs in the measurement object surface (i.e. a distortion with a sharply varying slope at each point of the cross section), this will appear as a large amount of deviation of the curvature data of the cross section from the reference value. Therefore, a portion with curvature data thereof being within the set permissible range can be determined not to be a distortion, whereas a portion with curvature data thereof exceeding the set permissible range can be determined to be a distortion.

That is, the distortion data extracting means 42 extracts, from among the curvature data, data over the upper limit value and data below the lower limit value as distortion data indicative of the distortion in that cross section.

As described above, by determining, from among the curvature data, data over the upper limit value and data below the lower limit value as distortion data indicative of the distortion in that cross section, it is possible to avoid extraction of unnecessary distortion data such as a too small distortion (i.e. an invisible distortion with a very gentle slope change at each point of the cross section).

And, a distortion degree evaluating means 46 evaluates a degree of distortion in a specific distorted region present in the measurement object surface, based on the three dimensional distortion data obtained over the measurement object surface.

Next, this evaluation of a distortion degree of a predetermined region in the measurement object surface effected by the distortion degree evaluating means 46 will be described in greater details.

FIG. 3 shows distortion data extracted by the distortion data extracting means 42 being shown in grey scale distribution according to magnitudes of values thereof. This can be displayed by a display device (not shown) connected to the distortion evaluating apparatus 40. That is, this FIG. 3 shows values exceeding the set permissible range and values below the set permissible range, from among the cross section curvature data. And, in the instant embodiment, as shown, there are developed the total of four distorted regions G1-G4 in the periphery of the attaching portion 2. And, in this embodiment, the width extension of the distorted region along the direction normal to each cross section (L-axis direction) is defined as a distortion length: L (FIG. 3 shows the distortion length L1 of the distorted region G1). A distortion length extracting means 44 is provided for automatically extracting the respective length of the specific distorted region such as the regions G1 through G4 described above, based on the three dimensional distortion data extracted by the distortion data extracting means 42.

FIG. 5 is a graph schematically showing curvature data for a plurality of respective cross sections and the upper limit values of the above-described set permissible range. Of the curvature data of the respective cross sections shown in FIG. 5, the data exceeding the upper limit values are the distortion data. And, the region exceeding the upper limit value for each cross section will be referred to as a cross sectional area: S1. Therefore, a region where a plurality of such cross sectional areas: S1 are present will be determined as a distorted region: Ga, Gb.

Then, a distortion volume extracting means 45 extracts the volume of each distorted region: Ga, Gb by multiplying the cross sectional areas: S1 for the respective cross sections over the distortion length L.

As described above, with use of the distortion length extracting means 44 and the distortion volume extracting means 45, the length and volume of a specific distorted region are extracted. And, with the distortion evaluating apparatus 40 relating to this embodiment, the distortion degree evaluating means 46 employs the combination of the length and the volume of the specific distorted region as distortion evaluation data and compares this distortion evaluation data with a predetermined evaluation reference data, thus evaluating the degree of the specific distortion. This evaluation reference data can be obtained empirically by comparing result of a human sensory evaluation on a specific distorted region and the distortion evaluation data comprising the length and the volume of the distorted region obtained according to the present embodiment as above.

FIG. 6 is a graph showing such result of comparison between the distortion evaluation data and evaluation reference data, plotting altogether distortion evaluation data extracted for 10 (ten) distorted regions by the distortion evaluating apparatus 40 of the invention. This graph showing comparison result can be displayed on a display device (not shown) to be connected to the distortion evaluating apparatus 40. In FIG. 6, the horizontal axis represents the distortion length whereas the vertical axis represents the distortion volume. And, for these ten (10) distorted regions, human sensory evaluations were carried out respectively therefor. And, the results of the sensory evaluations (from five points (good) to one point (poor)) are indicated with using different markers for the plottings thereof.

As shown in FIG. 6, with the distortion evaluating apparatus 40 of the present invention, the evaluation reference data are set such that the longer the distortion length and the greater the distortion volume, the lower (poorer) the evaluation of the degree of distortion in the distorted region. In FIG. 6, for the three distorted regions for which the human sensory evaluations provided poor results (from one to two points), similarly poor evaluation results were provided by the inventive distortion evaluating apparatus 40 also. On the other hand, for the seven distorted regions for which the human sensory evaluations provided good results (from three to five points), similarly good evaluation results were provided by the inventive distortion evaluating apparatus 40 also.

That is to say, with the distortion evaluating apparatus 40 of the present invention, the distortion degree evaluation effected by the distortion degree evaluating means 46 by using the combination of the length (i.e. the width extension of the distorted region) and the volume (i.e. the strength of the distorted region) as the distortion evaluation data and making comparison between this distortion evaluation data with the predetermined evaluation reference data is found to be consistent with the human sensory evaluation result.

As described above, the distortion evaluating apparatus 40 relating to the present embodiment effects a data processing operation which does not interpret curvature data with a small absolute value within a set permissible range as a distortion. And, this data processing is substantially equivalent to a sensory evaluation made by a human who finds a small distortion as permissible. That is to say, the above-described distortion data on which the result of distortion evaluation by the distortion evaluating apparatus 40 of this embodiment is based is analogous to the information on which the result of the human sensory evaluation is based.

Therefore, it may be said that a result of evaluation of distortion degree conventionally relied on a human sensor evaluation by a skilled artisan can now be quantitatively obtained by the distortion evaluating apparatus 40 of the present embodiment. Namely, a distortion which requires correction can be easily determined under a certain constant standard, whereby unnecessary distortion correction or unnecessary repetition of distortion correction can be avoided advantageously. Further, with using the distortion evaluating apparatus 40, a distortion which has developed on a body surface (e.g. a door panel surface of a motorcar) manufactured by press working can be discovered properly under the predetermined standard. Therefore, it is possible to make an appropriate correction on the mold used for this press working operation so as not to develop any distortion thereafter. That is, the distortion evaluating apparatus 40 of the invention can be utilized also for inspection of a mold to be used in press working.

Further, when an un-experienced human worker effects a sensory evaluation based on his/her sense, it is possible for this worker to make reference to the result of distortion evaluation quantitatively obtained by the distortion evaluating apparatus 40 which is equivalent to the result of human sensory evaluation made by an experienced artisan. That is to say, there is obtained a further advantage of providing the possibility of making reference to the quantitative evaluation result obtained by the distortion evaluating apparatus 40 for the purpose of allowing a less-skilled worker to develop his/her sensor skill so as to be able to obtain improved evaluation result.

Second Embodiment

A distortion evaluating apparatus 50 relating to the second embodiment differs from that the first embodiment in that the distortion degree evaluating means 46 employs the combination of the length and the area of a specific distorted region as the distortion evaluation data. Next, the distortion evaluating apparatus 50 according to the second embodiment will be described. The following discussion, however, will omit discussion of same or substantially same constructions as those of the first embodiment.

FIG. 7 shows a functional block diagram of the non-contact, three dimensional measurement system and distortion evaluating apparatus 50 relating to the second embodiment. The distortion evaluating apparatus 50 according to this second embodiment includes a distortion area extracting means 47 for extracting the area of a specific distorted region, and the distortion degree evaluating means 46 employs the combination of the length and the area of the specific distorted region as the distortion evaluation data and effects comparison between this distortion evaluation data and the evaluation reference data for evaluating the degree of distortion in the specific distorted region.

Like FIG. 5 described hereinbefore, FIG. 8 is a graph schematically showing curvature data for a plurality of respective cross sections and the upper limit value of the above-described set permissible range. There is shown a length of the portions intersecting with the upper limit value, i.e. a width: W of the distorted region. Then, the distortion area extracting means 47 obtains the area S2 of this specific distorted region by integrating the widths: W of the specific distorted region perpendicular to the length along the length direction (L-axis direction), based on the three dimensional distortion data extracted by the distortion data extracting means 42.

And, the distortion degree evaluating means 46 employs the combination of the length and the area of the specific distorted region as distortion evaluation data and compares this distortion evaluation data with a predetermined evaluation reference data, thus evaluating the degree of the specific distortion. FIG. 9 is a graph showing such result of comparison between the distortion evaluation data and evaluation reference data, plotting altogether distortion evaluation data extracted for 10 (ten) distorted regions by the distortion evaluating apparatus 50 of the invention. In FIG. 9, the horizontal axis represents the distortion length whereas the vertical axis represents the distortion area. And, for these ten (10) distorted regions, human sensory evaluations were carried out respectively therefor. And, the results of the sensory evaluations (from five points (good) to one point (poor)) are indicated with using different markers for the plottings thereof.

As shown in FIG. 9, with the distortion evaluating apparatus 50 of the present embodiment, like the first embodiment described above, the evaluation reference data are set such that the longer the distortion length and the greater the distortion area, the lower (poorer) the evaluation of the degree of distortion in the distorted region. The evaluation reference data can be obtained empirically by comparing the result of a human sensory evaluation on a specific distorted region and the distortion evaluation data comprising the length and the area of the distorted region obtained according to the present embodiment as above.

In FIG. 9, for the three distorted regions for which the human sensory evaluations provided poor results (from one to two points), similarly poor evaluation results were provided by the inventive distortion evaluating apparatus 50 also. On the other hand, for the seven distorted regions for which the human sensory evaluations provided good results (from three to five points), similarly good evaluation results were provided by the inventive distortion evaluating apparatus 50 also. That is to say, the distortion degree evaluation effected by the distortion degree evaluating means 46 of the inventive distortion evaluating apparatus 50 is found to be consistent with the human sensory evaluation result.

Other Embodiments

<1>

In the foregoing embodiments, the permissible range setting means 43 can variably set the reference value, the upper limit value and the lower limit value as desired. For instance, in FIG. 10 (*a*) shows an example setting in which of the set permissible range shown in FIG. 4 (*a*), the upper limit value is changed. For example, even if a distortion exists in the measurement object surface, if this exists at an inconspicuous part (e.g. a part where the cross section shape of the original measurement object surface is flat), the upper limit value and the lower limit value can be set smaller so as to allow even small curvature data to be extracted as distortion data.

Further, FIG. 10 (*b*) shows another example setting in which of the set permissible range shown in FIG. 4 (*b*), the reference value of a specific portion of the measurement object surface is changed. More particularly, the reference value is partially reduced. In this way, not only the upper limit value and the lower limit value, the reference value too can be changed. For instance, in case the curvature data is not zero as the original cross section shape of the measurement object surface is not flat, but curved, the secondary differential data (curvature data) of the original cross section shape of the measurement object surface can be set as the reference value.

As described above, the reference value, the upper limit value and the lower limit value can be set variably as desired, in accordance with various characteristics such as the designed original cross section shape of the measurement object surface.

<2>

In the foregoing embodiments, as shown in FIG. 6 and FIG. 9, respectively, with comparison between the distortion evaluation data and one evaluation reference data, the degree of distortion in a specific distorted region is evaluated in the two steps of "good" and "poor". Instead of this, the distortion evaluation data can be compared with a plurality of evaluation reference data set in a plurality of steps. And, the degree of distortion in a specific distorted region can be evaluated in a greater number of steps. For example, if two evaluation reference data are provided, another curve of the same shape as the evaluation reference data shown in FIG. 6 and FIG. 9 can be set in juxtaposition so as not to intersect with each other. With this, the degree of distortion of a specific distorted region can be evaluated in three steps of: "good", "acceptable" and "poor".

The distortion evaluating apparatus according to the present invention can utilized in quantitatively evaluating distortion in a body surface of a vehicle such as a motorcar. Therefore, as distortion which has developed in the body surface (e.g. a door panel surface of a motorcar) manufactured by press working can be discovered appropriately under a predetermined standard, it becomes possible to correct properly the mold used for this press working so as not to develop distortion thereafter. That is, the distortion evaluating apparatus of the invention can be utilized also for inspection of a mold to be used for press working.

Further, through accumulation of technique by repetition of such steps as designing of body shape, designing of mold, press working, distortion evaluation, correction of mold, it is possible to improve the prediction technique including CAE (computer-aided engineering) in designing a body shape and a mold which can effectively resist development of distortions therein.

Moreover, by utilizing the fact that the evaluation result of distortion degree is provided in the quantitative manner, the invention can be utilized for determination of whether a sensory evaluation of distortion degree by human sense is appropriate or not; that is, the invention can be utilized for technique heritance for educating a less-experienced human to a skilled artisan.

Figure 1:
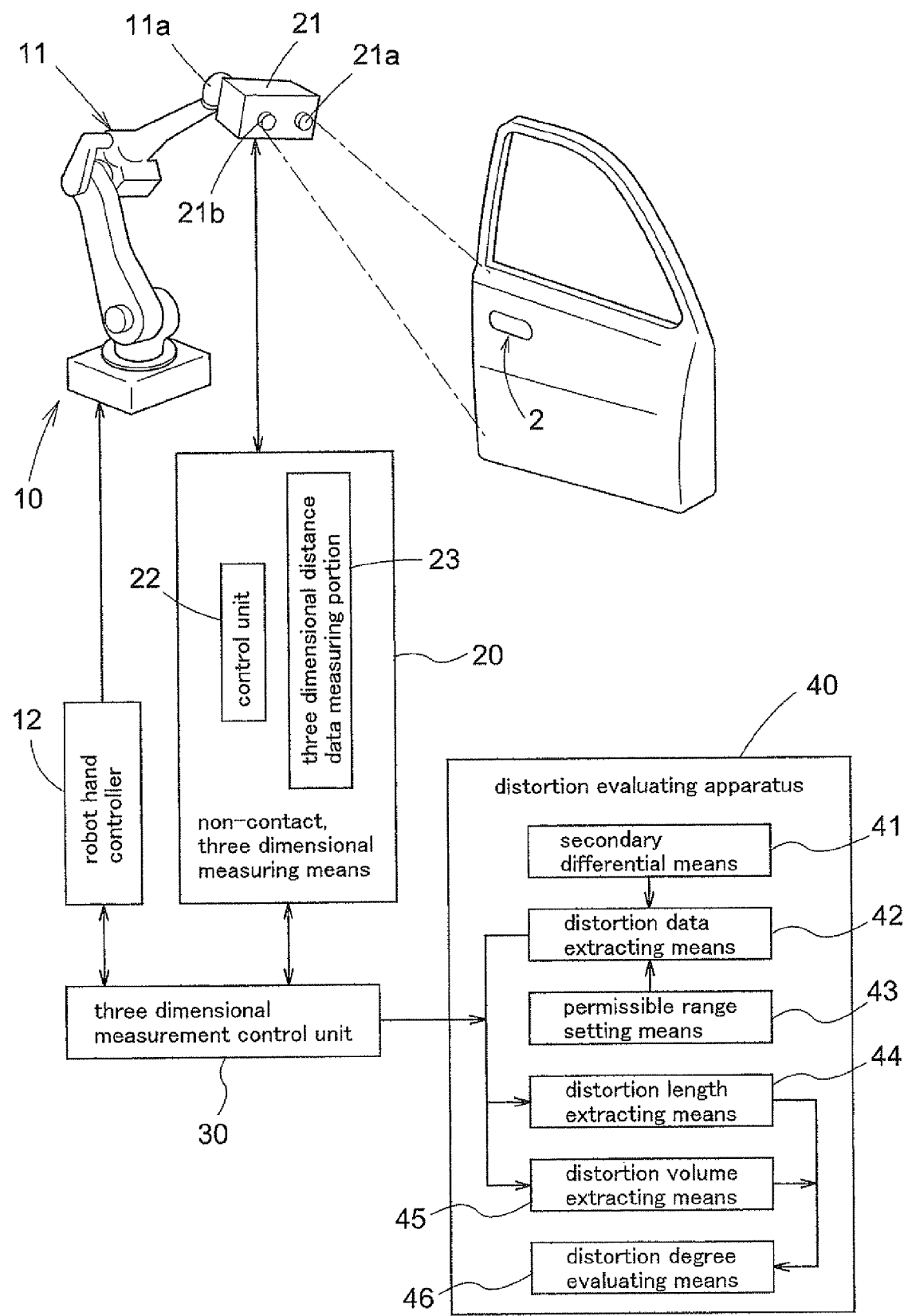
FIG. 1 a functional block diagram of a non-contact, three dimensional measurement system and a distortion evaluating apparatus according to a first embodiment, FIG. 2 an explanatory view of a photographic image obtained by a measuring head and a measurement image obtained from this photographic image, FIG. 3 a figure which draws cross section distortion data over a measurement object surface three dimensionally, FIG. 4 (*a*) a graph of a shape line at section A-A' in FIG. 3 and data obtained by effecting secondary differential operation on its two dimensional measurement data, (*b*) a graph of a shape line at section B-B' in FIG. 3 and data obtained by effecting secondary differential operation on its two dimensional measurement data, FIG. 5 a graph schematically showing curvature data of a plurality of respective cross sections and an upper limit value of a set permissible range, FIG. 6 a graph showing result of comparison between distortion evaluation data comprising combination of a length and a volume of a distorted region and evaluation reference data, FIG. 7 a functional block diagram of a non-contact, three dimensional measurement system and a distortion evaluating apparatus according to a second embodiment, FIG. 8 a graph schematically showing curvature data of a plurality of respective cross sections and an upper limit value of a set permissible range, FIG. 9 a graph showing evaluation reference data for evaluating distortion evaluation data comprising combination of a length and an area of a distorted region, and FIG. 10 graphs illustrating changes in the set permissible range.
Figure 2:
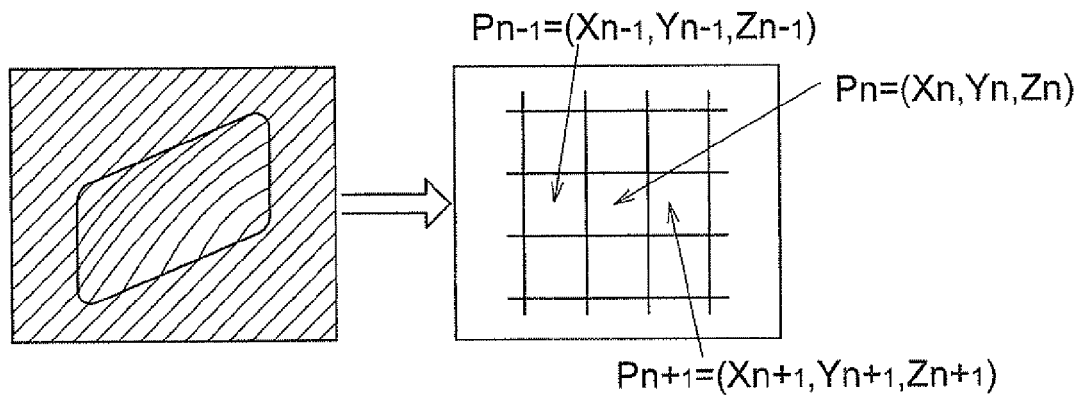
Figure 3:
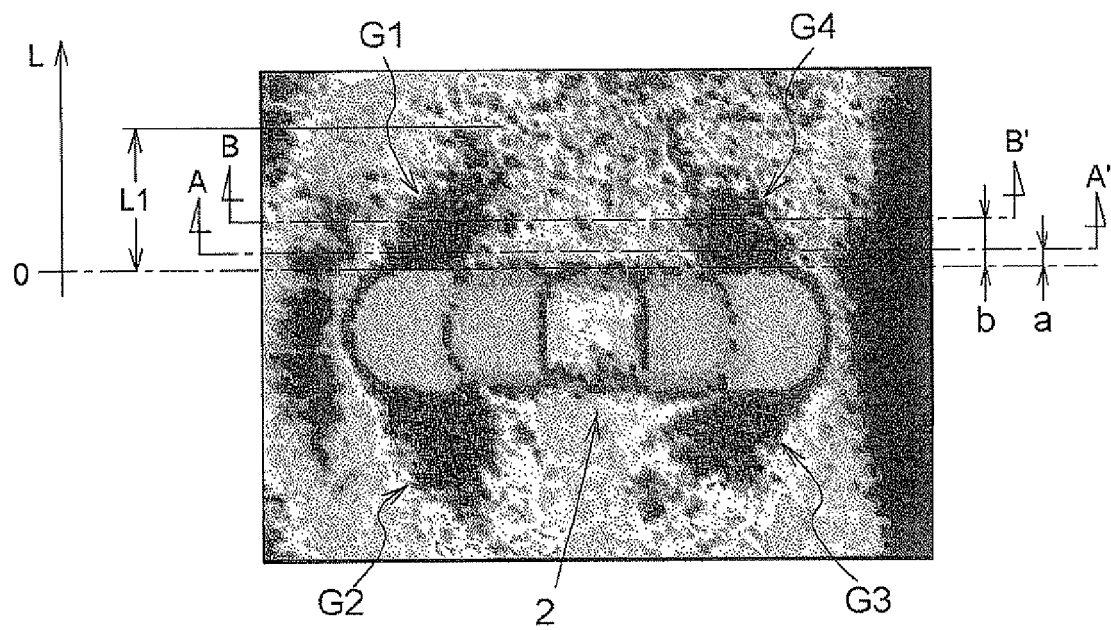
Figure 4:
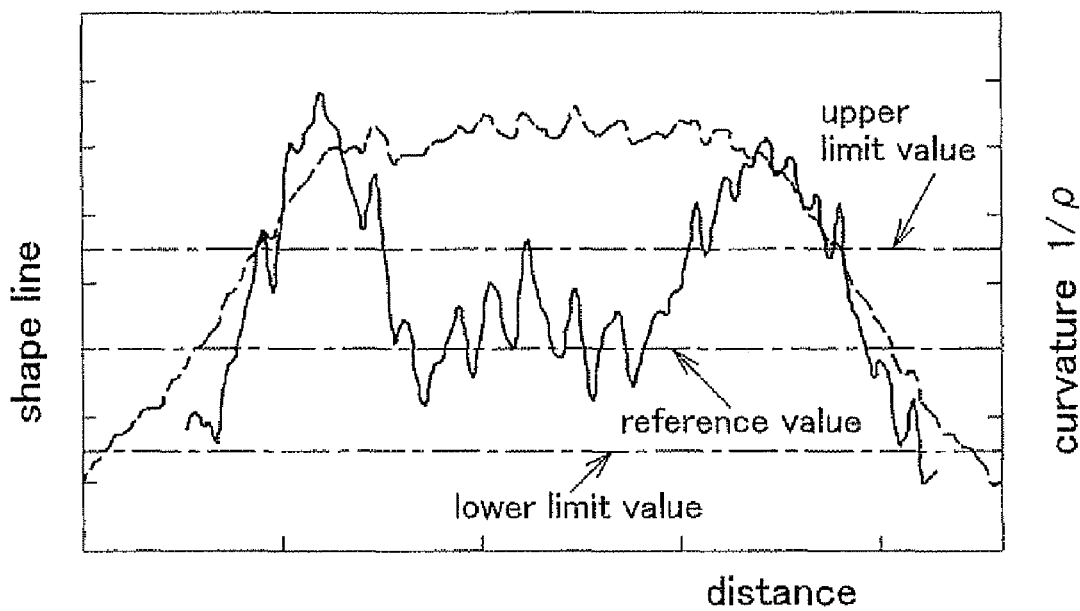
Figure 4:
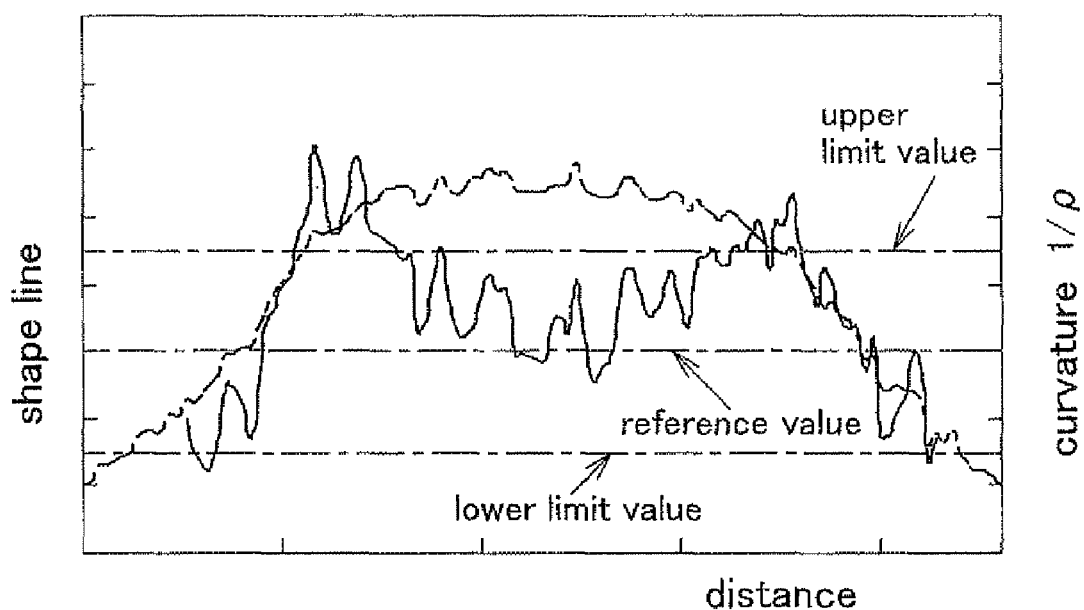
Figure 5:
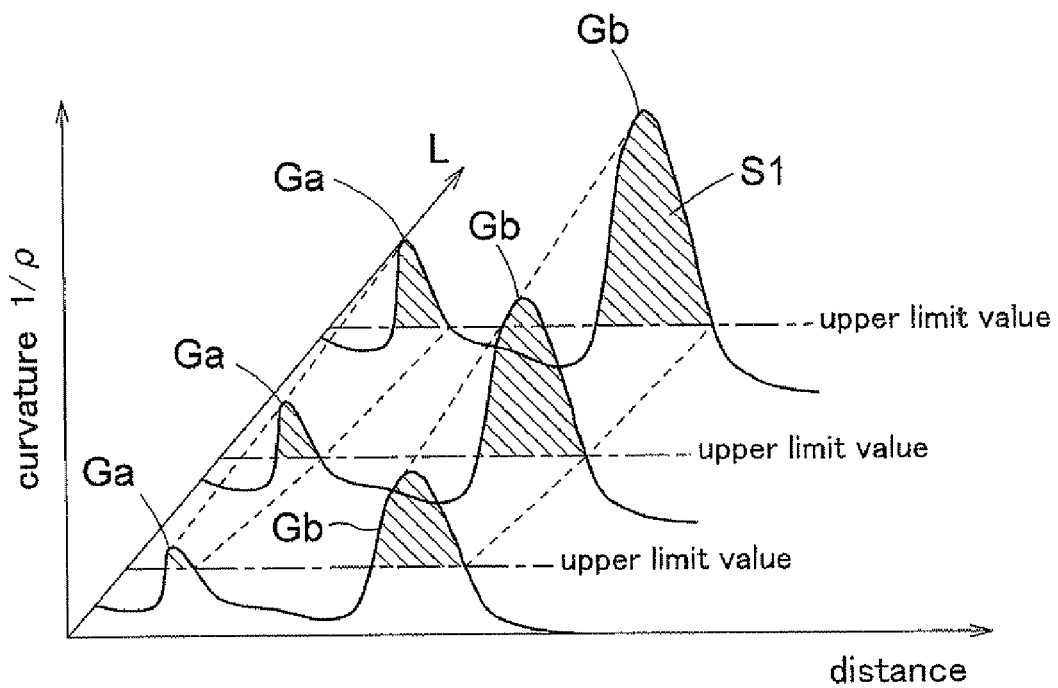
Figure 6:
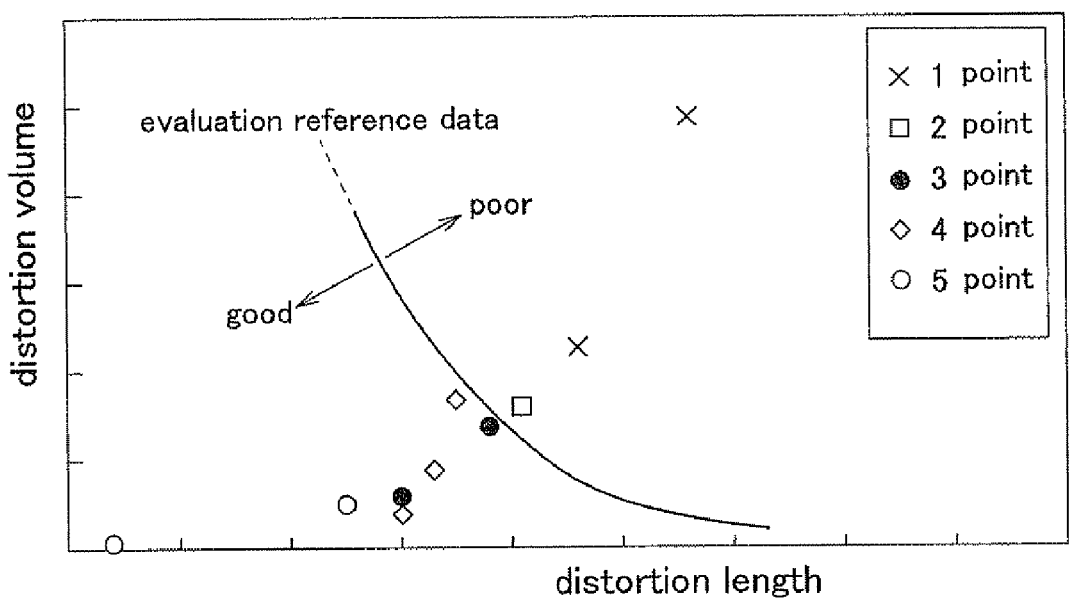
Figure 7:
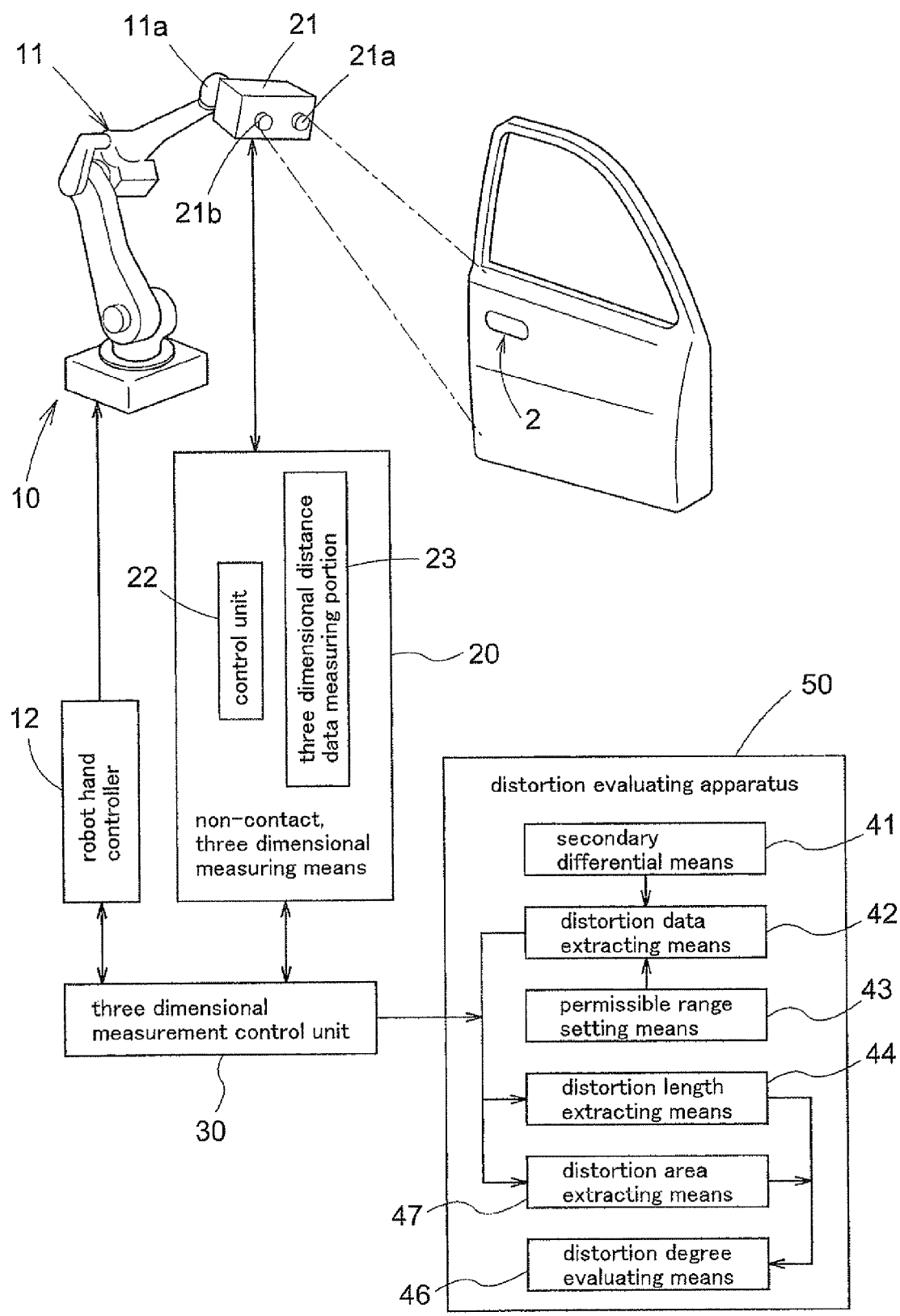
Figure 8:
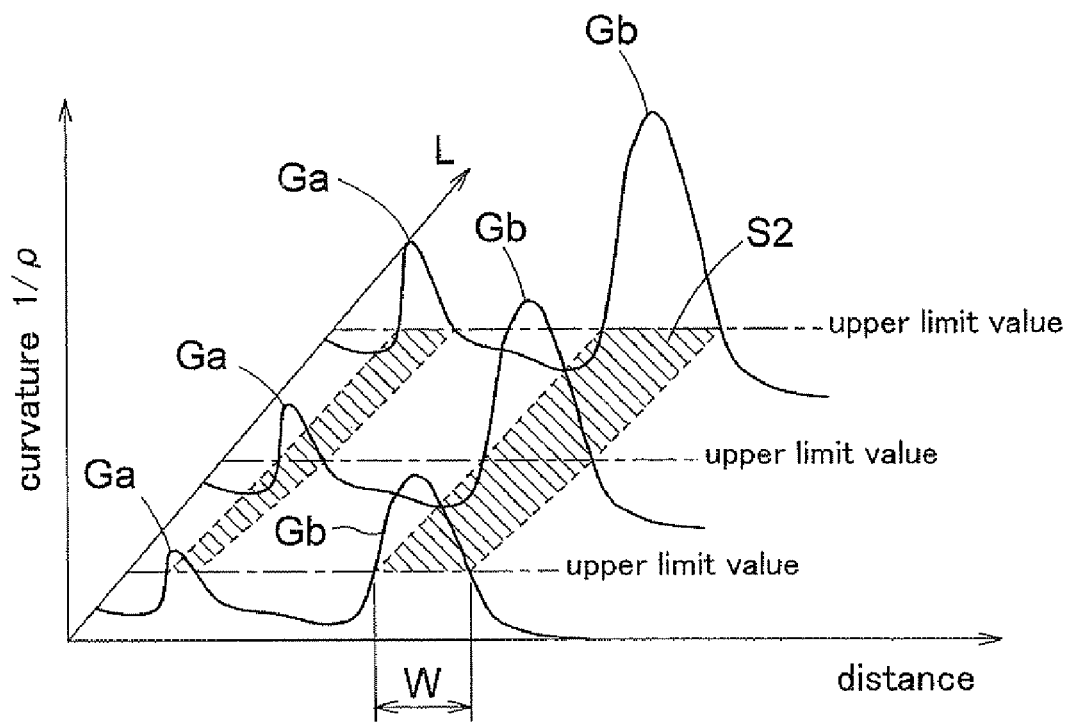
Figure 9:
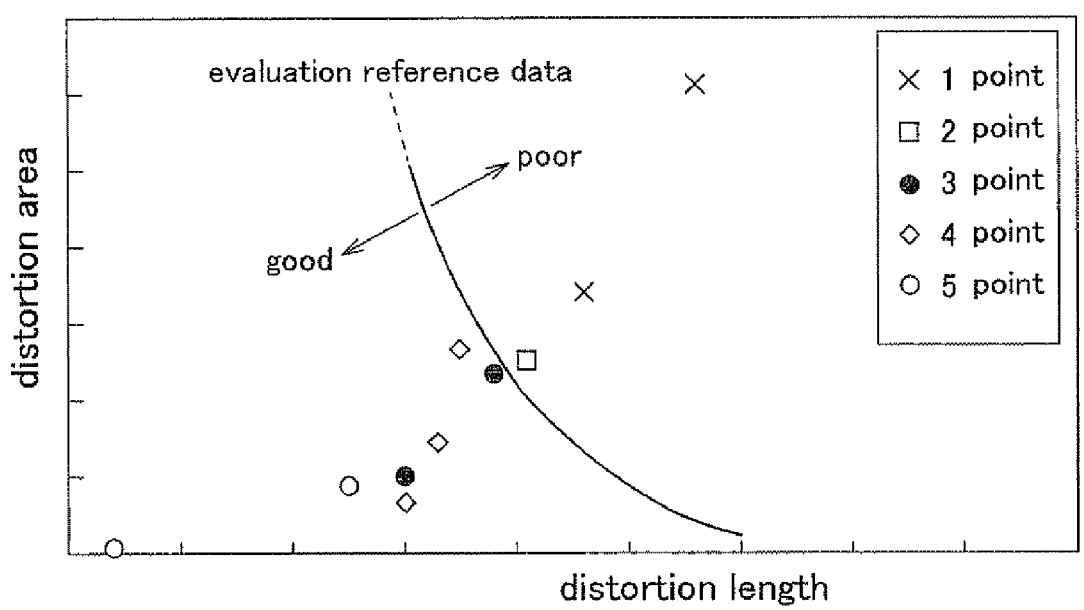
Figure 10:
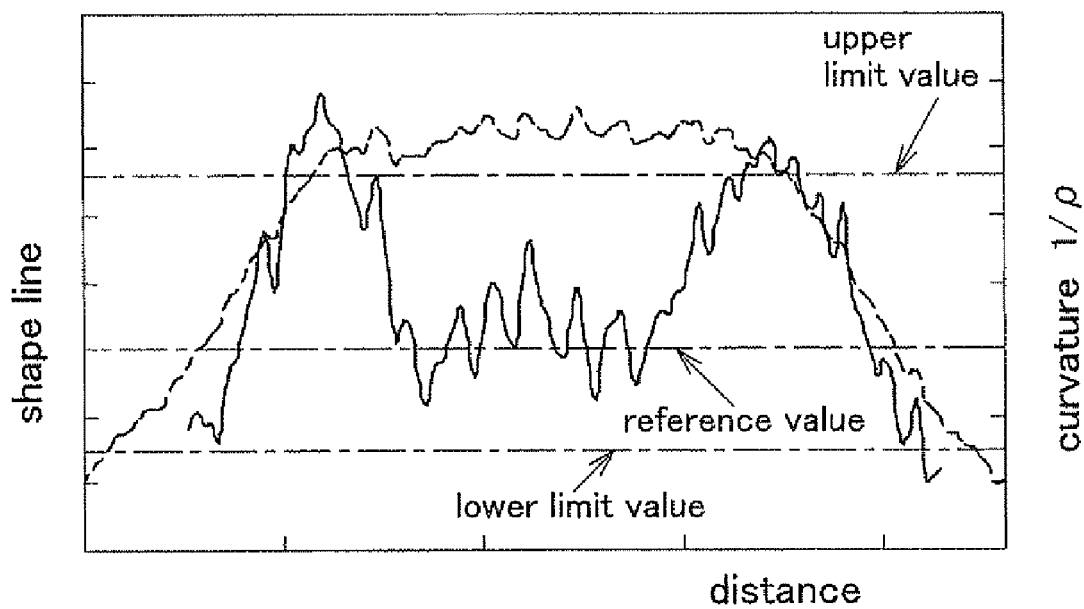
Figure 10:
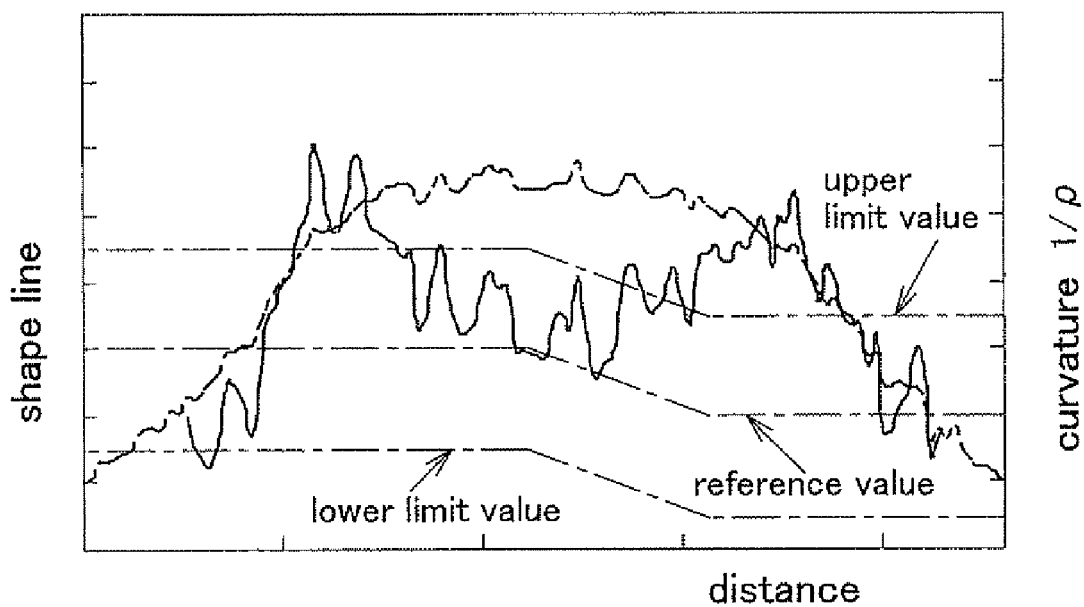

The invention claimed is:

1. A distortion evaluating apparatus for evaluating distortion based on three-dimensional measurement data obtained from a measurement object surface, the apparatus comprising:

a quadratic differential component configured for effecting a quadratic differential operation on two-dimensional measurement data of a cross section of the measurement object surface indicative of unevenness therein, thus obtaining curvature data for each one of a plurality of cross sections over the measurement object surface three-dimensionally;

a permissible range setting component configured for setting a permissible range for said curvature data, based on range of an upper limit value and a lower limit value from a reference value;

a distortion data extracting component configured for extracting a portion of said curvature data of the plurality of cross sections, over the measurement object surface three-dimensionally, exceeding said set permissible range as distortion data indicative of the distortion in the cross section;

a distortion length extracting component configured for extracting the length of a specific distorted region based on three-dimensional distortion data;

a distortion volume extracting component configured for extracting the volume of said specific distorted region based on the three-dimensional distortion data; and a distortion degree evaluating component configured for evaluating the degree of distortion in the specific distorted region present in the measurement object surface by using the combination of the length and the volume of the specific distorted region as distortion evaluation data and comparing evaluation reference data and the distortion evaluation data with each other.

2. The distortion evaluating apparatus according to claim 1, wherein said permissible range setting component changes at least one of said reference value, said upper limit value and said lower limit value, in accordance with characteristics of said measurement object surface.

3. A distortion evaluating apparatus for evaluation distortion based on three-dimensional measurement data obtained from a measurement object surface, the apparatus comprising:

a quadratic differential component configured for effecting a quadratic differential operation on two-dimensional measurement data of a cross section of the measurement object surface indicative of unevenness therein, thus obtaining curvature data for each one of a plurality of cross sections over the measurement object surface three-dimensionally;

a permissible range setting component configured for setting a permissible range for said curvature data, based on range of an upper limit value and a lower limit value from a reference value;

a distortion data extracting component configured for extracting a portion of said curvature data of the plurality of cross sections, over the measurement object surface three-dimensionally, exceeding said set permissible range as distortion data indicative of the distortion in the cross section;

a distortion length extracting component configured for extracting the length of a specific distorted region based on three-dimensional distortion data;

a distortion area extracting component configured for extracting the area of said specific distorted region based on the three dimensional distortion data by integrating widths of the specific distorted region perpendicular to the length along the direction of this length; and a distortion degree evaluating component for evaluating the degree of distortion in the specific distorted region present in the measurement object surface based on the three-dimensional distortion data by using the combination of said length and said area of the specific distorted region as distortion evaluation data and comparing evaluation reference data and said distortion evaluation data with each other.

4. The distortion evaluating apparatus according to claim 3, wherein said permissible range setting component changes at least one of said reference value, said upper limit value and said lower limit value, in accordance with characteristics of said measurement object surface.

5. A distortion evaluating method for evaluating distortion based on three-dimensional measurement data obtained from a measurement object surface, the method comprising the steps of:

providing a distortion evaluating apparatus comprising a quadratic differential component, a permissible range setting component, a distortion data extracting component, a distortion length extracting component, a distortion volume extracting component, and a distortion degree evaluating component;

effecting a quadratic differential operation on two-dimensional measurement data of a cross section of the measurement object surface indicative of unevenness therein, thus obtaining curvature data for each one of a plurality of cross sections over the measurement object surface three-dimensionally, using the quadratic differential component;

setting a permissible range for said curvature data, based on a range of an upper limit value and a lower limit value from a reference value, using the permissible range setting component;

extracting a portion of said curvature data of the plurality of cross sections, over the measurement object surface three-dimensionally, exceeding said set permissible range as distortion data indicative of the distortion in the cross section, using the distortion data extracting component;

extracting the length of a specific distorted region based on three dimensional distortion data, using the distortion length extracting component;

extracting the volume of said specific distorted region based on the three dimensional distortion data, using the distortion volume extracting component; and evaluating the degree of distortion in the specific distorted region present in the measurement object surface by using the combination of the length and the volume of the specific distorted region as distortion evaluation data and comparing evaluation reference data and the distortion evaluation data with each other, using the distortion degree evaluating component.

6. A distortion evaluating method for evaluating distortion based on three-dimensional measurement data obtained from a measurement object surface, the method comprising the steps of:

providing a distortion evaluating apparatus comprising a quadratic differential component, a permissible range setting component, a distortion data extracting component, a distortion length extracting component, a distortion area extracting component, and a distortion degree evaluating component;

effecting a quadratic differential operation on two-dimensional measurement data of a cross section of the measurement object surface indicative of unevenness therein, thus obtaining curvature data for each one of a plurality of cross sections over the measurement object surface three-dimensionally, using the quadratic differential component;

setting a permissible range for said curvature data, based on a range of an upper limit value and a lower limit value from a reference value, using the permissible range setting component; and extracting a portion of said curvature data of the plurality of cross sections, over the measurement object surface three-dimensionally, exceeding said set permissible range as distortion data indicative of the distortion in the cross section, using the distortion data extracting component;

extracting the length of a specific distorted region based on three dimensional distortion data, using the distortion length extracting component;

extracting the area of said specific distorted region based on the three dimensional distortion data by integrating widths of the specific distorted region perpendicular to the length along the direction of this length, using the distortion area extracting component; and evaluating the degree of distortion in the specific distorted region present in the measurement object surface based on the three dimensional distortion data by using the combination of said length and said area of the specific distorted region as distortion evaluation data and comparing evaluation reference data and said distortion evaluation data with each other, using the distortion degree evaluating component.

* * * * *

UNITED STATES PATENT AND TRADEMARK OFFICE
CERTIFICATE OF CORRECTION

PATENT NO. : 7,962,303 B2  Page 1 of 1
APPLICATION NO. : 12/064699
DATED : June 14, 2011
INVENTOR(S) : Seiji Oue et al.

It is certified that error appears in the above-identified patent and that said Letters Patent is hereby corrected as shown below:

Title Page, Item (57)

Column 2, Abstract, Line 14, after "extracting" delete "means"

Signed and Sealed this
Twenty-fifth Day of October, 2011

David J. Kappos
*Director of the United States Patent and Trademark Office*